United States Patent [19]
Siegel et al.

[11] Patent Number: 4,650,751
[45] Date of Patent: Mar. 17, 1987

[54] PROTECTED BINDING ASSAY AVOIDING NON-SPECIFIC PROTEIN INTERFERENCE

[75] Inventors: Richard C. Siegel, Yorktown Heights; Christina S. Marx, Peekskill, both of N.Y.

[73] Assignee: Technicon Instruments Corporation, Tarrytown, N.Y.

[21] Appl. No.: 490,063

[22] Filed: Apr. 29, 1983

[51] Int. Cl.$^4$ .................. G01N 33/53; G01N 33/546; G01N 33/78
[52] U.S. Cl. .......................... 435/7; 435/810; 436/175; 436/500; 436/501; 436/519; 436/533; 436/534; 436/808; 436/825
[58] Field of Search .............. 436/825, 500, 533, 534, 436/175, 501, 519, 808; 435/7

[56] References Cited
U.S. PATENT DOCUMENTS

| | | | |
|---|---|---|---|
| 4,032,626 | 6/1977 | Ward | 436/825 X |
| 4,225,576 | 9/1980 | Denning | 436/825 X |
| 4,362,531 | 12/1982 | de Steenwinkel | 436/825 X |
| 4,427,781 | 1/1984 | Masson | 436/825 X |
| 4,455,381 | 6/1984 | Magnusson | 436/825 X |
| 4,578,350 | 3/1986 | Armenta | 435/7 |

OTHER PUBLICATIONS

Chemical Abstracts, 97:68911f (1982).

Primary Examiner—Sidney Marantz
Attorney, Agent, or Firm—James R. Cartiglia; Edward H. Gorman, Jr.

[57] ABSTRACT

A specific binding enzyme-resistant ligand assay test material, which material comprises (a) a solid phase incorporated with one partner of a specific binding pair comprising said ligand or a binding analog thereof and a specific binding protein therefor; (b) a conjugate comprising the other partner of said specific binding pair incorporated with a substance which protects the specific binding protein of said pair from enzyme inactivation when bound with its partner; and (c) an active protein-inactivating enzyme. Also a specific binding method of assaying for an enzyme-resistant ligand in a sample, which method uses the above test material and which results in a reduction in interference caused by non-specific protein.

47 Claims, 8 Drawing Figures

PROTECTED BINDING ASSAY AVOIDING NON-SPECIFIC PROTEIN INTERFERENCE

BACKGROUND OF THE INVENTION

1. Field of the Invention

This invention relates to the field of specific binding assays, particularly to overcoming non-specific protein interference in agglutination assays of non-protein ligands. Agglutination assays are highly sensitive and used to determine a wide variety of substances. These assays have been embodied in commercially available test kits such as those used to detect triiodo-L-thyronine ($T_3$) and/or thyroxine ($T_4$).

2. Brief Description of the Prior Art

The development of specific binding assay techniques has provided extremely useful analytical methods for determining various organic substances of diagnostic, medical, environmental and industrial importance which appear in liquid mediums at very low concentrations. Specific binding assays are based on the specific interaction between a ligand, i.e., a bindable analyte under determination, and a binding partner therefor, i.e., receptor. Where one of the ligand and it binding partner is an antibody and the other is a corresponding hapten or antigen, the assay is known as an immunoassay.

These specific binding assays have been provided in a variety of solid state formats including analytical elements or test strips, coated tubes, particle-associated reagents and others. Agglutination assays are among the most widely used solid state specific binding assays, usually as immunoassays. They may be classified as direct, indirect (passive) or inhibition type agglutination assays. In a direct agglutination assay, particles having surface components which are one member of a specific binding pair (e.g., a receptor), are reacted with a sample to be assayed for the other member of the specific binding pair (e.g., ligand). In the indirect (passive) agglutination format, one member of a specific binding pair (e.g., receptor) is bound to a solid substrate particle, and this particle-bound member is reacted with a sample to be assayed for the other member of the pair (e.g., ligand). In inhibition-type agglutination assays, a sample to be tested for one binding pair member is first reacted with a solution containing the other member of the binding pair and this prereacted solution is then reacted with particles which contain (direct) or are bound with (indirect) the binding pair member suspected of being in the sample. Agglutination assays have been summarized in the literature. See, for example, Bellanti, *Immunology*, W. B. Saunders Co., Philadelphia (1971), pgs. 139 et seq; and Fudenberg, et al, *Basic & Clinical Immunology*, Lange Medical Publications, Los Altos, CA. (1976), pp. 308 et seq. Also, Sawai et al, U.S. Pat. Nos. 4,118,192 and 4,208,185 relate to agglutination assays. Earlier references which are likewise relevant are Singer et al, *J. Colloid and Interface Science*, 45:608–614 (1973) and Faure et al, *Protides of the Biological Fluids, Proceedings of the Colloquium*, 20:589–593 (1972). A number of agglutination assay test kits for specific analytes or ligands are commercially available and have also been described in the literature. See, for example, Rose, et al (Eds.), Manual of Clinical Immunology, American Society for Microbiology, Washington, D.C. (1978).

When assaying complex liquids, such as human serum, many non-specific proteins, such as lipoproteins and autoantibodies, inhibit the agglutination reaction. Therefore, these proteins must be destroyed to obtain accurate measurement of ligand concentrations. The prior art has thus far required a pretreatment procedure separate from the assay. For Example, Kobayashi, et al, *Steroids*, 34:829–834 (1979), discloses a direct fluorescence polarization immunoassay of serum cortisol in which non-specific serum protein binding of fluorescent-labeled hapten (cortisol) was eliminated by sodium dodecyl sulfonate (SDS). The SDS was not removed prior to performing the assay.

Non-specific protein interference in assays for non-protein ligands can be overcome by first digesting the proteins using a proteolytic enzyme such as pepsin. The enzyme is then inactivated or destroyed prior to the assay. For example, Collet-Cassart, et al *Clin. Chem.*, 27:1205–09 (1981) disclose a particle-counting immunoassay (PACIA) for digoxin in samples which were pre-digested with pepsin. The digestion was stopped by adding tris(hydroxymethyl)methylamine which inactivates the pepsin. See also Chau et al, J. Clin. Endocrinol. Metab., 42:189–192 (1976).

Agglutination assays so far available, including those for the determination of $T_3$ and $T_4$, have suffered from non-specific protein interference. Invariably, it has been necessary to perform preliminary procedures to overcome this source of interference. Thus, despite the efforts reflected in the above references, no one has met the problem of providing a specific binding agglutination assay which avoids the effects of this interference without the need for pretreatment.

SUMMARY OF THE INVENTION

In accordance with the present invention, specific binding assays are provided in which the effects of non-specific protein interference are avoided or overcome without the need for pretreatment steps. As such, it is now possible to provide a homogeneous immunoassay format in which this interference has been overcome and which is particularly suitable for use in automated analysis systems.

These advantages are achieved by the specific binding enzyme-resistant ligand assay test material of the present invention, which material comprises (a) a solid phase incorporated with one partner of a specific binding pair comprising said ligand or a binding analog thereof and a specific binding protein therefor; (b) a conjugate comprising the other partner of said specific binding pair incorporated with a substance which protects the specific binding protein of said pair from enzyme inactivation when bound with its partner; and (c) an active protein-inactivating enzyme.

The invention further provides a specific binding method of assaying for an enzyme-resistant ligand in a sample, which method consists essentially of the steps of: (i) combining said sample in a reaction mixture with (a) a solid phase incorporated with one partner of a specific binding pair comprising said ligand or a binding analog thereof and a specific binding protein therefor; (b) a conjugate comprising the other partner of said specific binding pair incorporated with a substance which protects the specific binding protein of said pair from enzyme inactivation when bound with its partner; and (c) an active protein-inactivating enzyme; and (ii) detecting any resultant binding in said same reaction mixture.

Various embodiments, which include or use the method are also contemplated. For example, the test material can be provided as part of a test kit. The kit comprises the packaged combination of one or more containers of or devices incorporated with the components of the test material in any of a variety of physical formats.

DESCRIPTION OF THE PREFERRED EMBODIMENTS

Preferred embodiments of the present invention include a particle-associated agglutination assay reagent composition, a test kit comprised of containers or devices, each incorporated with one or more components of the test composition, in packaged combination with other components or materials and methods of using the test composition and kit of the invention. Specific terms in the following description which refer only to a particular embodiment are exemplary of all of the embodiments unless otherwise indicated.

Sample fluids on which tests are performed include biological, physiological, industrial, environmental, and other types of liquids. Of particular interest are biological fluids such as serum, plasma, urine, cerebrospinal fluid, saliva, milk, broth and other culture media and supernatants as well as fractions of any of them. Physiological fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluid which are tested by conventional methods are contemplated as within the meaning of this term as used and can, likewise, be assayed in accordance with the invention.

In the context of this invention, the term "ligand" refers to any substance, or class of related substances, which are not susceptible to protein-inactivating enzymes and whose presence is to be qualitatively or quantitatively determined in a sample fluid, such as those just described. The present assay can be applied to the detection of any such ligand for which there is a specific binding partner and, conversely, to the detection of the capacity of a liquid medium to bind such a ligand (usually due to the presence of a binding partner for the ligand in the sample). The ligand usually is an organic molecule for which a specific binding partner exists or can be developed. The ligand, in functional terms is usually selected from antigens, haptens, hormones, vitamins, metabolites and pharmacological agents and their receptors and binding substances. Specific examples of ligands which can be detected using the present invention are hormones such as thyroxine ($T_4$) and triiodothyronine ($T_3$); antigens and haptens such as ferritin, bradykinin, prostaglandins, and tumor specific antigens; vitamins such as biotin, vitamin $B_{12}$ folic acid, vitamin E, vitamin A, and ascorbic acid; metabolites such as 3', 5'-guanosine monophosphate, pharmacological agents or drugs such as aminoglycoside antibiotics like gentamicin, amikacin and sisomicin, or drugs of abuse such as the opium alkaloids and ergot derivatives.

The tems "specific binding protein" or "receptor" refer to any substance, or class of substances, which has a specific binding affinity for the ligand to the exclusion of other substances. In the majority of embodiments, the present invention will incorporate specific binding assay reagents which interact with the ligand or its binding capacity in the sample in an immunochemical manner. That is, there will be an antigen-antibody or hapten-antibody relationship between reagents and/or the ligand or its binding capacity in the sample. Such assays therefore are termed immunoassays and the special interaction between the ligand and its receptor, or binding partner, is an immunochemical binding. The use of either polyclonal or monoclonal antibodies is contemplated. Additionally, it is well understood in the art that other binding interactions between the ligand and the binding partner serve as the basis of specific binding assays, including the binding interactions between hormones, vitamins, metabolites, and pharmacological agents, and their respective receptors and binding substances. For example, polypeptide hormone receptors as binding agents or partners are discussed in Langan, et al, (Eds.) *Ligand Assay*, Masson Publishing U.S.A. Inc., New York, pages 211 et seq. (1981).

The "active protein-inactivating enzyme" of the present invention refers to any enzyme which is effective to negate the chemical or biological properties of a protein, usually an endogenous protein, which causes it to produce non-specific interference effects on specific binding agglutination assay reactions. The use of such enzymes in reducing or eliminating these interfering effects has been described in pretreatment of samples apart from the actual assay procedures. Any of the enzymes so described or having a substantially similar effect can be used. These primarily include proteolytic enzymes such as trypsin, pepsin, chymotrypsin, carboxypeptidase and mixtures of proteases such as Pronase mixed enzyme preparation (Calbiochem-Behring Corp., LaJolla, CA). Such protein inactivating enzymes are discussed at length in Perlmann & Lorand (Eds.), Methods in Enzymology-Proteolytic Enzymes (Vol. XIX), Academic Press, N.Y. (1970).

The terms "solid state" or "solid phase" of the present invention can take on a multitude of forms, and is therefore intended as being broad in context. It can be mono- or multi-phasic, comprising one or more appropriate materials or mediums of similar or different absorptive or other physical characteristics. It can be hydrophobic or hydrophilic, bibulous or nonporous. In its most efficient embodiment the solid phase can be carefully tailored to suit the characteristics of the particular specific binding assay system to be employed.

In one embodiment the solid phase is a matrix or surface capable of being incorporated with specific binding assay reagents. It can take on many known forms such as those utilized for chemical and enzymatic solution analysis. Solid phase test devices have been applied to specific binding assays. A commonly used solid phase device comprises a nonporous surface, such as the interior surface of a test tube or other vessel, to which antibody is affixed or coated by adsorption or covalent coupling. Likewise, devices for use in specific binding assays wherein the antibody reagent is fixed to a matrix held in a flow-through column are known (U.S. Pat. Nos. 4,036,947; 4,039,652; 4,059,684; 4,153,675; and 4,166,102). U.S. Pat. Nos. 3,826,619; 4,001,583; 4,017,597; and 4,105,410 relate to the use of antibody coated test tubes in radioimmunoassays. Solid phase test devices have also been used in enzyme immunoassays (U.S. Pat. Nos. 4,016,043 and 4,147,752) and in fluorescent immunoassays (U.S. Pat. Nos. 4,025,310 and 4,056,724; and British Patent Spec. No. 1,552,374). The use of such heterogeneous specific binding assay test devices is exemplified by the method of U.S. Pat. No. 4,135,884. The test device is incorporated with the antibody reagent and is brought into contact with the liquid sample and with the remaining reagents of the reaction system. After an incubation period, the solid phase device is physically removed from the reaction solution and the label measured either in the solution or on the test device. In one preferred embodiment the element can be in the form of a test slide, made from a material such as polystyrene, which has been molded to have at least one reaction well, usually centrally disposed therein. The well usually has a diameter of from about 1.0 to about 2.5 centimeters (cm) and has a depth of from about 1.0 to about 10 millimeters (mm), preferably from about 2 mm to about 6 mm.

The most preferred solid phase format is particulate. As previously noted, particle-associated agglutination assays include those assays using particles having specific binding pair members as surface components or substrate particles to which such components have been bound. These substrate particles preferably range in size from about 0.1 to about 5.0 microns in diameter, with bacterial substrate particles usually ranging from about 1 to about 3 microns in diameter. Substrate particles which have been used as carriers of specific binding pair members include eucaryotic red blood cells (unaltered or tanned), siliceous earth (e.g., bentonite), latex, and procaryotic particles (e.g., bacterial cells). The so-called latex particles consist normally of a synthetic polymeric material such as polystyrene. Other suitable organic polymers include butadiene, styrene-butadiene copolymers, acrylic polymers or mixtures thereof. Procaryotic particles such as bacterial or fungal cells or virus particles have also been widely used as substrate particles in agglutination assays. Among the bacteria used as substrate particles are those from the genus Staphylococcus, particularly *Staphylococcus aureus* (*S. aureus*). For example, *S. aureus* (Cowan I type) has been bound, through protein A molecules extending from the cell wall surface to a binding partner.

Many organic molecules will readily adhere by non-covalent adsorption to such substrate particles. For example, red blood cells (erythrocytes) readily absorb many polysaccharides. Also, the protein A in *S. aureus*, Cowan I strain, specifically binds to the Fc locus of certain immunoglobulins. For the attachment of proteins, however, it is usually necessary to first treat the particles or covalently link the proteins, such as through linking groups. Linking groups which have been used include bis-diazo-benzidine, glutaraldehyde and 1,3-difluoro-4,6-dinitrobenzene. Others are discussed in Fudenberg, et al, (Eds.), Basic & Clinical Immunology, Lange Medical Publications, Los Altos, CA., pg. 310 (1976).

The "substance which protects the specific binding protein" of the specific binding pair from enzyme inactivation when bound with its partner is contemplated as being any natural or synthetic molecule which is not, itself, suspectible to the protein-inactivating enzyme and can sequester, disguise, preferentially bind or otherwise associate with the specific binding protein to render it insusceptible to the protein-inactivating enzyme. Substances which can be used for this purpose include large molecules which sterically protect the binding protein from enzyme attack when bound. Exemplary of such large molecules are high molecular weight polymers like dextran or Ficoll, (Pharmacia Fine Chemicals, Inc., New Market, NJ) which is a polymeric product of the reaction between epichlorohydrin and sucrose.

The test material of the invention includes a conjugate comprising the binding partner for the species associated with the solid phase, whether it be specific binding protein or ligand, incorporated with a substance which protects the specific binding protein of the pair from enzyme inactivation when bound with its partner. The conjugate is formed using conventional organic synthesis techniques which do not impair or alter the specificity of the binding partner which it includes.

Although it is not a theory on which the invention must be predicated, at least one mechanism for the unexpected agglutinated binding protein protection results achieved can be described. In all cases there is a solid phase incorporated with one partner of a specific binding pair comprising the ligand or a binding analog thereof and a specific binding protein therefor. In the mechanism postulated here the conjugate comprises the other partner of said specific binding pair, which has an avidity and is present in a concentration which together provide a first association rate, incorporated with a substance that protects the specific binding protein of said pair from enzyme inactivation when bound with its partner and the active protein-inactivating enzyme has an avidity and is present in a concentration which together provides a second association rate which is less than the first association rate.

In accordance with this and other possible mechanisms the specific binding protein, e.g., antibody, is present in the reaction mixture in a concentration of at least about 0.04 percent (%) weight volume (w/v), and preferably from about 0.04 percent (w/v) to about 0.07 percent (w/v). Likewise, the protein inactivating enzyme is present in a concentration of not more than about 4.0 milligrams per milliliter (mg/ml), and preferably from about 2.0 to about 4.0 mg/ml. One example of this is a specific binding assay composition or material which includes (a) a particle-associated thyroxine or triiodothyronine antibody in a concentration of from about 0.04 to about 0.07 percent (w/v); (b) trypsin in a concentration of from about 2.0 to about 4.0 mg/ml; and (c) a conjugate as described above in a concentration of from about 0.22 to about 0.88 micrograms per milliliter (ug/ml).

The following working examples describe experiments which were performed in developing the present invention. Standard commercially available reagent grade chemicals were used whenever possible.

EXAMPLE I

THYROXINE PROTECTED BINDING ASSAY

Measurement of total serum thyroxine ($T_4$) is the single most important test for determining thyroid function. The normal $T_4$ range is 4.5 to 12.0 micrograms/deciliter (ug/dl); however, the test must be able to detect concentrations as low as 1.0 ug/dl and as high as 24.0 ug/dl. This is necessary to accurately identify those patients who have thyroid disorders. This Example reports experiments which demonstrate a nonisotopic, homogeneous $T_4$ immunoassay in accordance with the invention.

Antisera Preparation

Antibody to $T_4$ was induced in New Zealand white rabbits by an intradermal primary injection of 400 ug of a conjugate which was $T_4$ covalently coupled to bovine serum albumin (BSA) emulsified in an equal volume of Freund's complete adjuvant. Secondary booster immunizations contained 400 ug of $T_4$-BSA conjugate emulsified in an equal volume of incomplete Freund's adjuvant and were administered once a month. The animals were bled three times a week.

Antibody Purification

Antibody specific for $T_4$ was isolated by immunoadsorbtion. The immunoadsorbent consisted of $T_4$ covalently bound to Sepharose 4B (Pharmacia Fine Chemicals, Piscataway, NJ). This material was prepared using the bisoxirane method described by Sundberg and Porath in *J. Chromatog.*, 90:87–98 (1974). Five milliliters (ml) of the immunoadsorbent were packed on top of 25 ml of Sephadex G-25 (Pharmacia, supra) in a 2×20 centimeter (cm) glass chromatography column. Five ml of antisera, prepared as described above, were applied to the column and allowed to enter the column until the red or amber color reached the immunoadsorbent-Sephadex interface. The antisera was allowed to remain in contact with the adsorbent for an additional 30 minutes at room temperature. The immunoadsorbent was then washed with two column volumes of barbital buffered saline (0.05M barbital, 0.15M NaCl, 0.1% $NaN_3$, pH 8.6) followed by a quantity of borate buffered saline (0.04M borate, 0.15M NaCl, 0.1% $NaN_3$, pH 8.1) sufficient to bring the absorbence of the effluent at 280 nanometers (nm) to less than 0.01. At this point the adsorbed antibody was eluted with 1.0M acetic acid. The eluant was collected in 1 ml aliquots with a fraction collector. Those fractions with an absorbence at 280 nm greater than 0.1 and a pH greater than 7.0 were pooled and stored at −20° centrigrade (C.) until used. Typically 1–2 milligrams (mg) of purified antibody were isolated from 1 ml of antisera.

Antibody Sensitized Latex Preparation

Purified antibody, described above, is coupled to chloromethyl styrene latex by a modification of the method described in Masson, et al, *Methods In Enzymology*, 79:106–109 (1981). A preparation using the above described antibodies in the method exactly as described by Masson, et al, ibid. can also be used.

$T_4$-Ficoll Conjugate Preparation $T_4$ was covalently coupled to cyanogen bromide activated Ficoll 400 (Pharmacia, supra). One hundred milligrams (mg) of Ficoll was dissolved in 6 ml of 0.4M $K_2CO_3$ and the pH was adjusted to 11.0. The solution was rapidly stirred and three, fifty ul additions of cyanogen bromide solution (333 mg/ml in N,N-dimethylformamide) were made. The pH of the Ficoll solution was maintained at 11.0 by the addition of 2N NaOH. Each addition of cyanogen bromide was made within one minute of the previous addition and after the last addition the solution was incubated for four minutes. The pH was then dropped to 10.0 with 2N HCl and 0.5 ml of a $T_4$ solution was added (80 mg/ml in N,N-dimethylformamide made alkaline with 11–15 drops of 0.4M $K_2CO_3$). The reaction mixture was stirred for two hours at room temperature then dialyzed exhaustively against 0.01M $Na_2HPO_4$ (pH 9.0). Typically, 60–70 moles of $T_4$ were incorporated into each mole of Ficoll.

$T_4$-Ficoll Conjugate/Trypsin Reagent Preparation $T_4$-Ficoll conjugate, prepared as described above, polyethylene glycol, 8000 (J. T. Baker Chemical Co., Phillipsburg, NJ), Tween-20 (Technicon Instruments Corp., Tarrytown, NY), $CaCl_2$, and bovine pancreatic trypsin (Sigma Chemical Co., St. Louis, MO) were mixed such that the final concentrations were 1.2 ug/ml, 3.76% (w/v), 0.11% (v/v), 1 mM, and 7.3 mg/ml, respectively, in barbital buffered saline (pH 8.6).

Antibody Sensitized Latex Reagent Preparation

Antibody sensitized latex, prepared as described above, 8-anilino-1-naphthalenesulfonic acid (Eastman Kodak Co., Rochester, NY), Tween-20 and Ficoll 400 were mixed in a buffer consisting of 0.035M carbonate, 0.015M barbital, 0.15M sodium chloride and 0.1% sodium azide (pH 9.7), such that the final concentrations were 0.17% (w/v), 0.103 mg/ml, 0.11% (v/v/), and 0.86 mg/ml, respectively.

Reference Method

The reference method was a solid phase coated tube Gamma Coat ™ radioimmunoassay (RIA) (Clinical Assays, Division of Travenol Laboratories, Inc., Cambridge, MA) and was used according to the manufacturer's directions.

Assay Procedure and Results

The assay of the present invention may be performed using a spectrophotometer or an automated clinical chemistry analyzer. A Technicon RA-1000 ™ instrument system was used for most of the results reported here. In each of the experiments described below the assay was initiated by adding 26 ul of test serum, control or standard to 175 ul of $T_4$-Ficoll/trypsin reagent. The reaction mixture was then incubated for two minutes at 37° C. before adding 175 ul of antibody sensitized latex reagent. The complete reaction mixture was incubated for an additional minute, then the absorbance at 600 nm was recorded at 15 second intervals for two minutes. The rate of change of absorbance was determined by least squares fitting of the absorbance and time data. This slope was inversely proportional to the concentration of $T_4$ in the test sample. Log/logit transformation of the data produced linear standard curves which were then used to analyze unknowns, as described below.

As an initial step, $T_4$-Ficoll dependent protection of bound antibody was demonstrated. Antibody sensitized latex reagent, $T_4$-Ficoll/trypsin reagent, and a serum-based standard without $T_4$ were mixed in a 0.5 centimeter (cm) quartz cuvette. The cuvette was placed in a Beckman DU-8 spectrophotometer (Beckman Instruments, Inc., Fullerton, CA) and the absorbance at 600 nm was monitored as a function of time. The rate of agglutination is directly proportional to the rate of change in the optical density, as noted in Faure, et al, *Protides of the Biological Fluids,* 20:589–593 (1972), and Singer, et al, *Journal of Colloid and Interface Science,* 45:608–614 (1973). The data shown in FIG. 1 demonstrates a rapid increase in optical density that begins to plateau after about a ten minute incubation period. These particles remained agglutinated even after overnight incubation.

Figure 2:
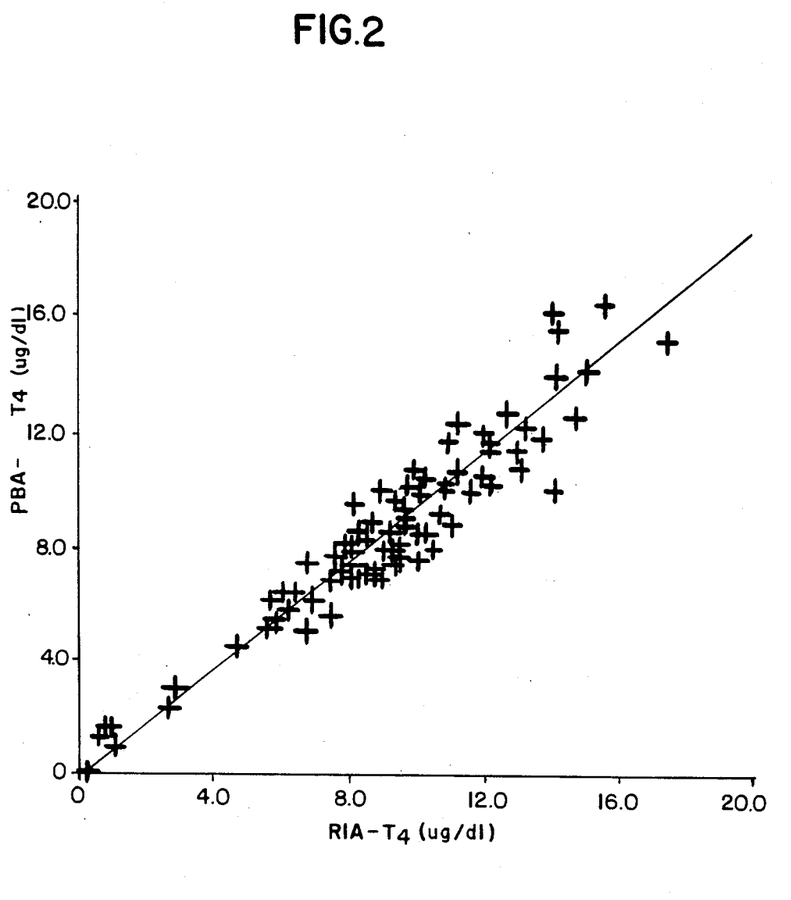
FIG. 2 is a scatter plot of the correlation between the $T_4$ protected Binding Assay of the invention and a reference radioimmunoassay method, based on the experiments of Example I.

Next, one hundred three (103) human sera were analyzed by the method of the invention, automated with a Technicon RA-1000 instrument system, and by the RIA reference procedure described above to determine the degree with which the results from the two methods correlated. The data are shown in FIG. 2. The correlation data were analyzed by orthogonal linear regression and are summarized below.

Correlation Between Thyroxine Protected Binding Assay and RIA

| N | Mean X | Mean Y | Slope | Y-Intercept | V |
|---|---|---|---|---|---|
| 103 | 9.3 ug/dl | 8.6 ug/dl | 0.96 | −0.26 ug/dl | 0.94 |

Figure 3:
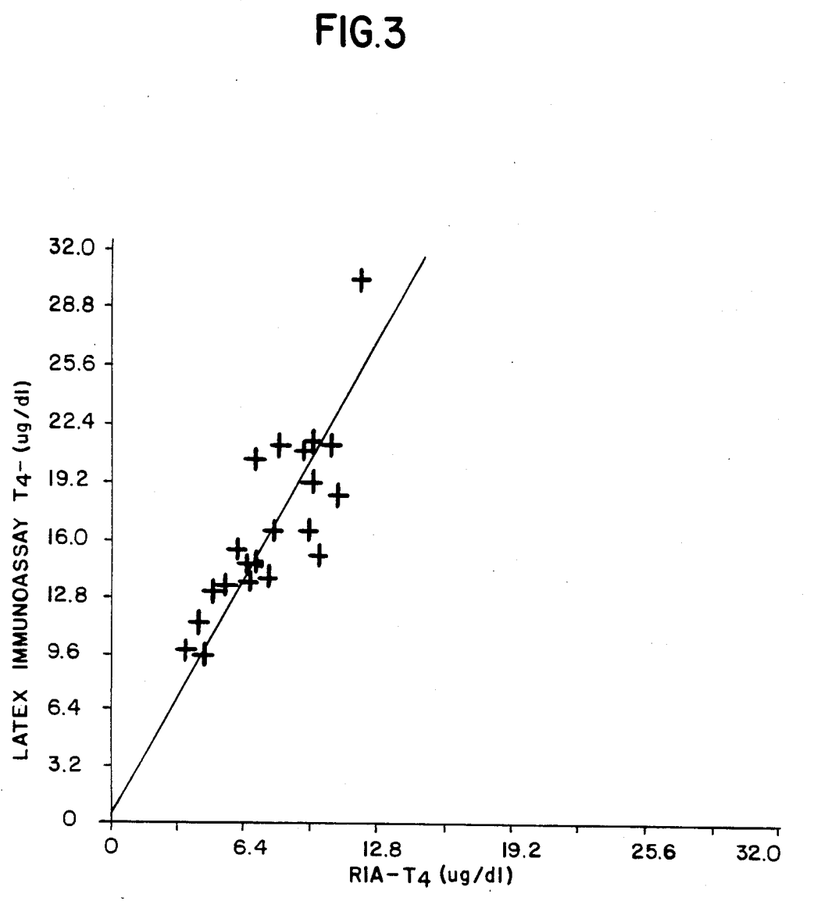
FIG. 3 is a scatter plot of the correlation between a conventional $T_4$ agglutination assay which did not include trypsin and a reference radioimmunoassay method, also based on the experiments of Example I.

For purposes of comparison with the above, 21 human sera were analyzed as decribed above for the present invention with the exception that trypsin was not included in the reaction mixture. The data are shown in FIG. 3 and summarized below.

Correlation of Prior Art Latex Immunoassay and RIA

| N | Mean X | Mean Y | Slope | Y-Intercept | V |
|---|---|---|---|---|---|
| 21 | 7.8 ug/dl | 16.2 ug/dl | 2.08 | 0.02 ug/dl | 0.82 |

Conclusion

Figure 1:
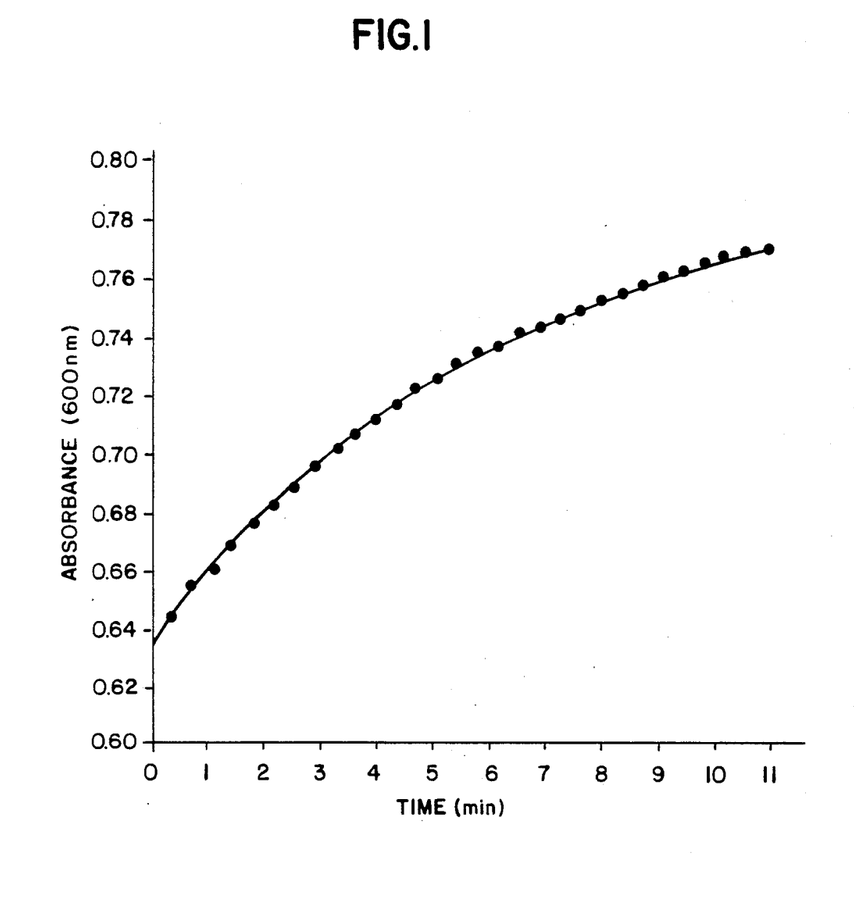
FIG. 1 is a graphical illustration of the protection of specific binding protein in an agglutination complex, achieved by the Protected Binding Assay (PBA) of the invention, based on the change in absorbance over time set forth in the experiments of Example I.

The data shown in FIG. 1 demonstrate that specific antibody-latex/$T_4$-Ficoll agglutinates will form and persist in the presence of high concentrations of trypsin. One possible explanation for this observation is that the combination of $T_4$-Ficoll with the antibody-latex sterically inhibits the approach of the proteolytic enzyme and prevents the enzyme from degrading the antibody.

The improvement in the method brought about by including a proteolytic enzyme, such as trypsin, in the reaction mixture is demonstrated by the difference between FIGS. 2 and 3. As shown in FIG. 3, in the absence of trypsin the values produced by the latex immunoassay were about twice as high as the reference method. This was due to non-specific serum interference and resulted in serum samples having erroneously elevated values. This non-specific interference was destroyed by trypsin as demonstrated in FIG. 2, which shows excellent correlation between the latex immunoassay with trypsin and the reference method.

EXAMPLE II

USE OF $T_4$-DEXTRAN IN THE $T_4$ PROTECTED BINDING ASSAY

The experiments reported here compare the use of $T_4$-Dextran with the use of $T_4$-Ficoll conjugate. The antisera preparation, antibody purification, antibody sensitized latex and antibody sensitized latex reagent preparations, $T_4$-Ficoll conjugate and $T_4$-Ficoll conjugate/trypsin reagent preparations, analytical procedure used were identical to those described in Example I.

$T_4$-Dextran Conjugate Preparation $T_4$ was covalently coupled to cyanogen bromide activated Dextran, T500 (Pharmacia, supra) using exactly the same procedure as described for $T_4$-Ficoll in Example I.

$T_4$-Dextran Conjugate/Trypsin Reagent Preparation $T_4$-Dextran, polyethylene Glycoll 8000, Tween-20, $CaCl_2$, and bovine pancreatic trypsin were mixed such that the final concentrations were 1.0 ug/ml, b 3.76% (w/v), 0.11% (v/v), 1 mM, and 7.3 mg/ml, respectively. All of the materials were dissolved in barbital buffered saline (pH 8.6).

Figure 4:
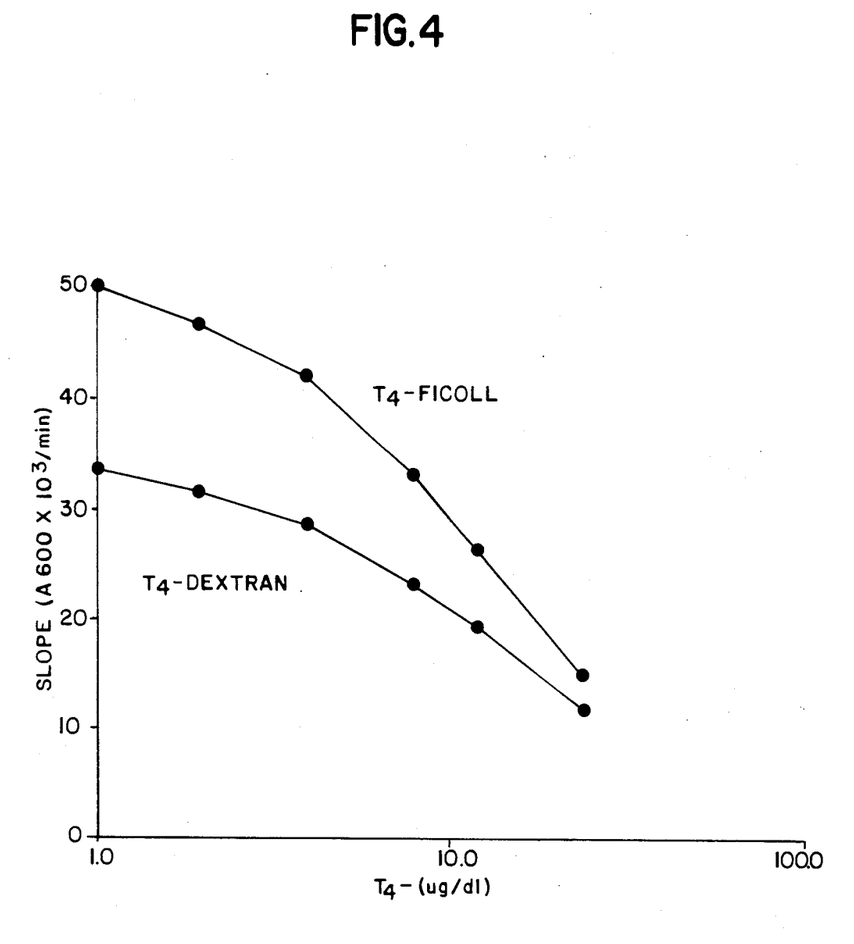
FIG. 4 is a graphic illustration of the absorbance at various $T_4$ levels using the Protected Binding Assay of the invention incorporating either $T_4$-Ficoll or $T_4$-Dextran conjugates, based on the experiments of Example II.

Assay Procedure and Results $T_4$ standard curves were measured using the Technicon RA-1000 instrument system and either $T_4$-Ficoll or $T_4$-Dextran. The data shown in FIG. 4 indicate that both $T_4$-Ficoll and $T_4$-Dextran function as "protectors" in this $T_4$ binding protection latex immunoassay. Larger signal changes were observed with $T_4$-Ficoll than with $T_4$-Dextran. However, the signal obtained with $T_4$-Dextran is increased by raising the polyethylene glycol concentration.

Conclusion

Both $T_4$-Dextran and $T_4$-Ficoll function in the antigen protection latex immunoassay and produce appropriate dose response curves. High molecular weight non-protein molecules constitute and effective class of materials for this purpose.

EXAMPLE III

USE OF CHYMOTRYPSIN IN THE $T_4$ PROTECTED BINDING ASSAY

The experiments reported here compare the use of chymotrypsin as the proteolytic enzyme with the use of trypsin. The antisera preparation, antibody purification, antibody sensitized latex and antibody sensitized latex reagent preparations, $T_4$-Ficoll conjugate and $T_4$-Ficoll conjugate/trypsin reagent preparations, and analytical procedure used were identical to those described in Example I.

T4-Ficoll Conjugate/Chymotrypsin Reagent Preparation

The reagent was prepared exactly as described in Example I for the T4-Ficoll conjugate/trypsin reagent, except that bovine pancreatic 2-chymotrypsin (Sigma Chemical Co., supra) was included in the reagent at a final concentration of 7.3 mg/ml.

Assay Procedure and Results

Twenty-one human sera were analyzed by the antigen protection latex immunoassay using the Technicon RA-1000 instrument system in the presence of either trypsin or chymotrypsin. The data are presented by the scatter plot in FIG. 5, and analyzed by orthogonal linear regression below.

Figure 5:
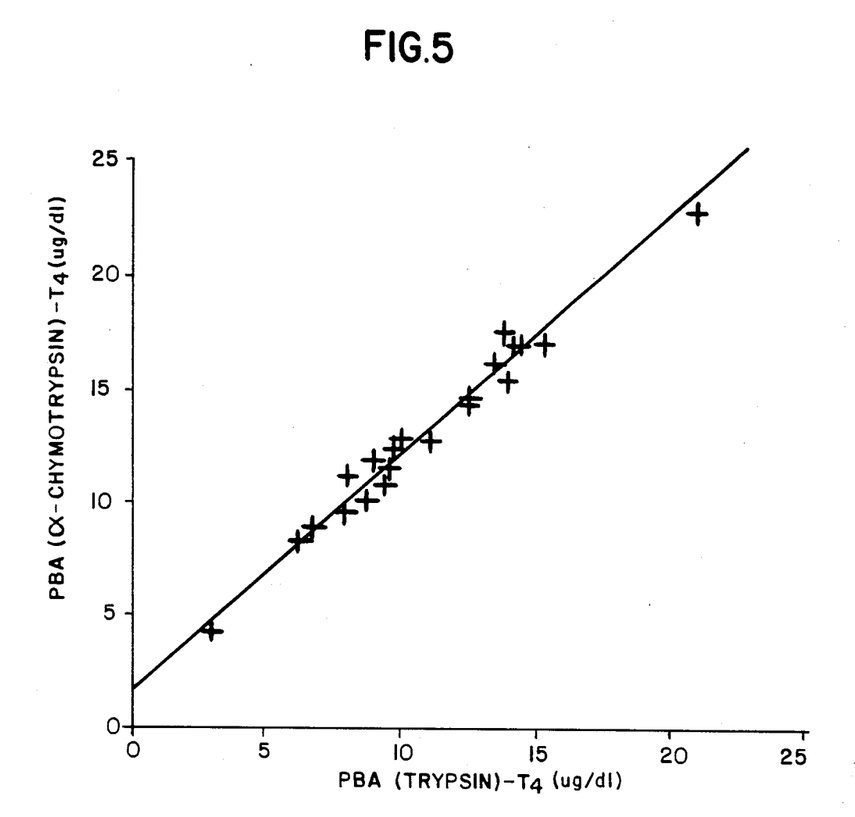
FIG. 5 is a scatter plot of the correlation between the $T_4$ Protected Binding Assay of the invention using either trypsin or chymotrypsin as the only modification, as based on the experiments of Example III.

Effect of Chymotrypsin in the $T_4$ Protected Binding Assay

| N | Mean X | Mean Y | Slope | Y-Intercept | V |
|---|--------|--------|-------|-------------|------|
| 21 | 11.1 ug/dl | 13.1 ug/dl | 1.02 | 1.72 ug/dl | 0.99 |

Conclusion

Chymotrypsin may be used in place of trypsin in the Protected Binding Assay of the invention. As shown in FIG. 5, equivalent results were obtained when either trypsin or chymotrypsin were included in the reaction mixture. The T4-Ficoll provided protection for bound antibody against the proteolytic effects of chymotrypsin, yet the chymotrypsin digested serum proteins in such a way that non-specific interactions with the latex particle were eliminated and correct T4 values were produced.

EXAMPLE IV

USE OF PRONASE IN THE $T_4$ PROTECTED BINDING ASSAY

The experiments reported here compare the use of Pronase (B Grade, Calbiochem-Behring Corp., LaJolla, CA) proteolytic enzyme mixture with the use of trypsin. The antisera preparation, antibody purification, antibody sensitized latex and antibody sensitized latex reagent preparations, T4-Ficoll conjugate and T4-Ficoll conjugate/trypsin reagent preparations, and analytical procedure used were identical to those described in Example I.

T4-Ficoll Conjugate/Pronase Reagent Preparation

This reagent was prepared exactly as described in Example I for the T4-Ficoll conjugate/trypsin reagent, except that Pronase was included in the reagent at a final concentration of 7.3 mg/ml.

Assay Procedure and Results

Twenty-one human sera were analyzed by the antigen protection latex immunoassay, using a Technicon RA-1000 instrument system, in the presence of either trypsin or Pronase. The data are presented by the scatter plot in FIG. 6 and were analyzed by orthogonal linear regression below.

Figure 6:
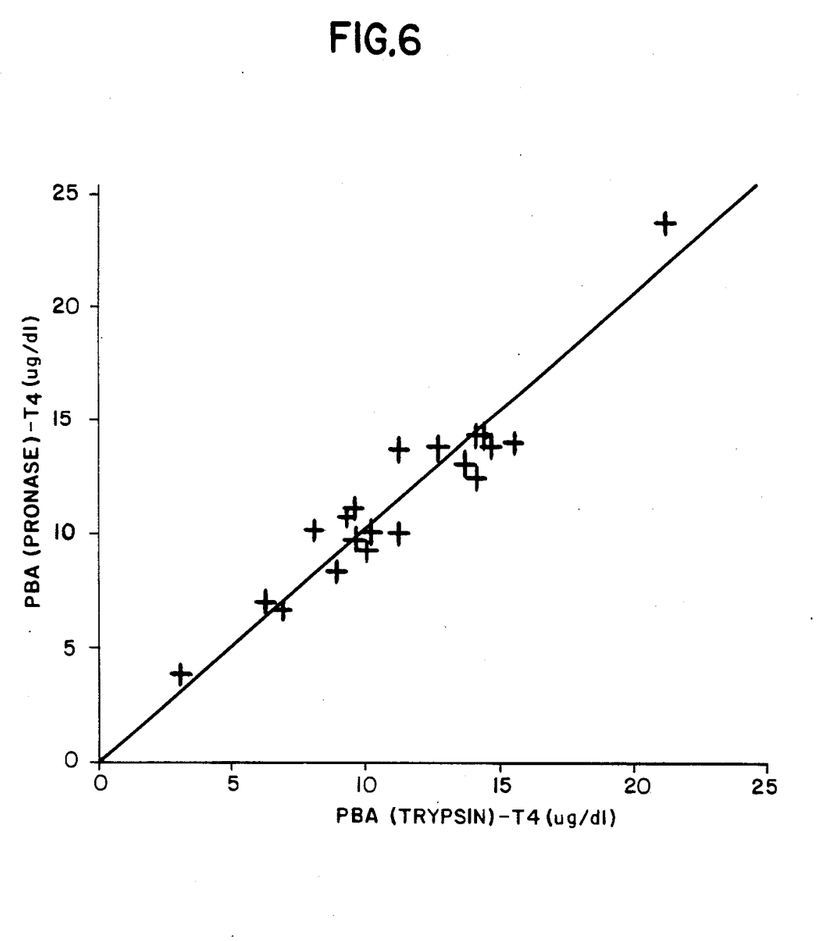
FIG. 6 is a scatter plot of the correlation between the $T_4$ Protected Binding Assay of the invention using either trypsin or Pronase as the only modification, based on the experiments of Example IV.

Effect of Pronase on the $T_4$ Protected Binding Assay

| N | Mean X | Mean Y | Slope | Y-Intercept | V |
|---|--------|--------|-------|-------------|------|
| 21 | 11.2 ug/dl | 11.6 ug/dl | 1.02 | 0.07 ug/dl | 0.95 |

Conclusion

Pronase may be used in place of trypsin in the Protected Binding Assay of the invention. As shown in FIG. 6, equivalent results were obtained when either trypsin or Pronase was used in the assay. Both enzymes produced about the same average value of T4, 11.2 ug/dl for trypsin and 11.6 ug/dl for Pronase, and the slope of the correlation plot was 1.02. The T4-Ficoll in the reaction mixture protected the antibody from proteolytic degradation by trypsin, yet destroyed those proteins that interfered in the measurement of T4.

EXAMPLE V

THEOPHYLLINE PROTECTED BINDING ASSAY

Theophylline (1,3-dimethylxanthine) is commonly used in the treatment of bronchial asthma. The serum concentration of the drug must be closely monitored since the drug has a narrow therapeutic range of 10–20 ug/ml while drug concentrations in excess of 20 ug/ml may be toxic. The experiments reported below demonstrate that the antigen protection latex immunoassay of the invention can be used to accurately and precisely quantitate serum levels of theophylline.

Antisera Preparation

Rabbit anti-theophylline antisera were purchased from Kallestad, Austin, TX.

Antibody Purification

Antibody was isolated by ammonium sulfate precipitation. Antisera was mixed in equal volumes with saturated ammonium sulfate solution which had been previously adjusted to pH 8. The solution was stirred at 4° C. for two hours and the precipitated antibody was then isolated by centrifugation. The pellet was washed twice with a volume of 50% saturated ammonium suflate, pH 8.0, that was equal to the original volume of antiserum. The precipitate was then solubilized in a volume of borate buffer saline (pH 8.1) that was equal to the original volume of antiserum. The antibody solution was then exhaustively dialyzed against borate buffered saline (pH 8.1) and clarified by centrifugation. The isolated antibody was stored at −20° C. until used.

Antibody Sensitized Latex Preparation

Purified antibody, described above, is coupled to chloromethyl styrene latex by a modification of the method described in Masson, et al, *Methods in Enzymology*, 74:106–139 (1981). A preparation using the above-described antibodies in the method exactly as described by Masson, et al, ibid. can also be used.

Synthesis of 8-E Carboxypropyl Theophylline

8-E carboxypropyl theophylline was synthesized exactly as described in Cook et al, *Research Communications in Chemical Pathology and Pharmacology*, 13:497–505 (1976).

Synthesis of N-(2-aminoethyl)Carbamylmethylated-Ficoll

N-(2-aminoethyl)carbamylmethylated-Ficoll (AECM-Ficoll) was synthesized exactly as described in Inman, *J. Immunol.* 114:704–709 (1975).

Theophylline-Ficoll Conjugate Preparation

8-E carboxypropyltheophylline was covalently coupled to AECM-Ficoll using a carbodiimide coupling. Twenty-three mg of 1-(3-Dimethyl amino-propyl)-3-ethylcarbodiimide hydrochloride (Aldrich Chemical Co., Metuchen, NJ) was added to 10 mg of 8-E-carboxypropyl-theophylline dissolved in 1 ml of N,N-dimethylformamide. The solution was allowed to activate for 40 minutes at room temperature, then 320 ul of this solution was added to 0.5 ml of a 10 mg/ml solution of AECM-Ficoll dissolved in 0.1M carbonate buffer (pH 6.3). The reaction mixture was incubated overnight at 4° C. Excess reagents were removed by sequential dialysis against 3 liters of of 0.1M sodium acetate buffer (pH 4.5), 2 liters of 0.1M sodium carbonate buffer (pH 9.5), 2 liters of borate buffered saline (pH 8.1) and again against 2 liters of fresh borate buffered saline (pH 8.1). Sixty to seventy moles of theophylline were incorporated into each mole of AECM-Ficoll.

Theophylline-Ficoll Conjugate/Trypsin Reagent Preparation

Theophylline-Ficoll conjugate, prepared as decribed above, Tween-20, $CaCl_2$ and bovine pancreatic trypsin were mixed such that the final concentrations were 1.25 ug/ml, 0.1% (v/v), 1 mM, and 6 mg/ml, respectively, in borate buffered saline (pH 8.1).

Antibody Sensitized Latex Reagent Preparation

Antibody sensitized latex, prepared as described above, and Tween-20 were mixed in borate buffered saline (pH 8.1) containing 0.1% (w/v) bovine serum albumin. The final concentration of the antibody sensitized latex was 0.12% (w/v) and the Tween-20 was 0.1% (v/v).

Reference Method

The reference method was the Emit-aad theophylline assay (Syva, Palo Alto, CA) and was used according to the manufacturer's direction.

Assay Procedure and Results

The assay of the present invention may be performed using either a spectrophotometer or an automated clinical chemistry analyzer. A Technicon RA-1000 TM instrument system was used for all of the results reported here. The assay was initiated by adding 2 ul of test serum, control or standard to 200 ul of antibody sensitized latex reagent. The reaction mixture was then incubated for 15 seconds at 37° C. before adding 200 ul of theophylline-Ficoll/trypsin reagent. The complete reaction mixture was incubated for an additional 30 seconds at 37° C., then the absorbance at 600 nm was recorded at 15 second intervals for two minutes. The rate of change of absorbance was determined by least-squares fitting of the absorbance and time data. This slope was inversely proportional to the concentration of theophylline in the test sample. Log/logit transformation of the data produced linear standard curves which were then used to analyze unknowns.

Figure 7:
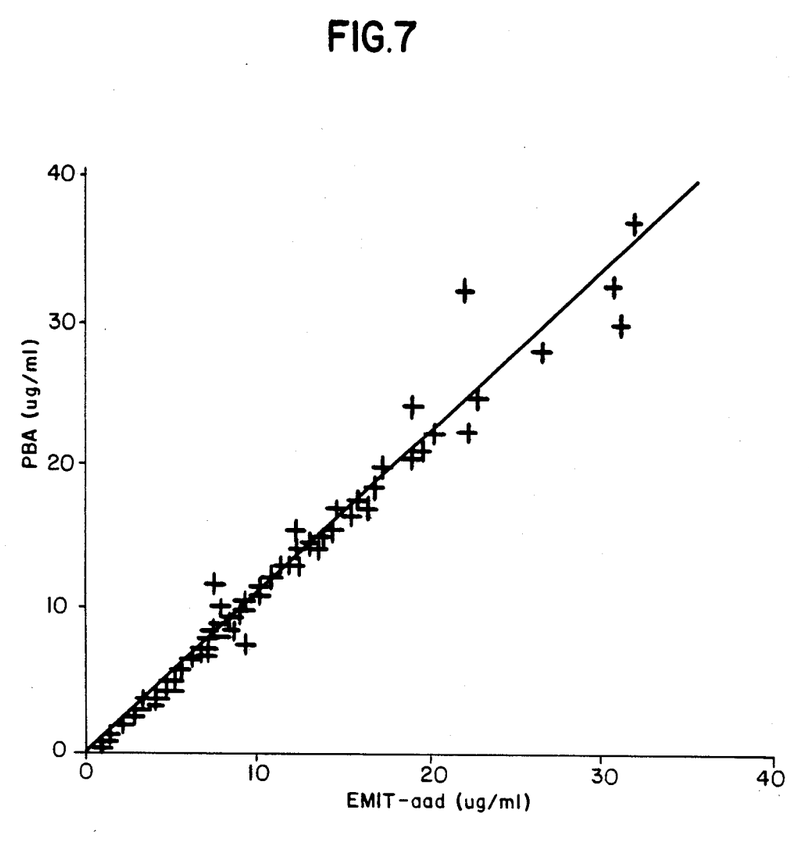
FIG. 7 is a scatter plot of the correlation between the theophylline Protected Binding Assay of the invention and a reference method, based on the experiments of Example V.

Eighty-one human sera were obtained from patients being treated with theophylline. These sera were analyzed by the method of the present invention employing the Kallestad polyclonal antibody and by the Syva Emit reference method to determine the degree with which the results from the two methods correlated. The data are shown in FIG. 7. The correlation data were analyzed by orthogonal linear regression and are summarized below.

Correlation Between the Theophylline Protected Binding Assay and Emit

| N | Mean X | Mean Y | Slope | Y-Intercept | V |
|---|--------|--------|-------|-------------|------|
| 81 | 10.6 ug/ml | 11.5 ug/ml | 1.09 | −0.06 ug/ml | 0.99 |

Conclusion

The correlation data indicate excellent agreement between the theophylline protected binding immunoassay and the reference method. The average value produced by the present method, 11.5 ug/ml, is almost identical to the average value produced by the reference method, 10.6 ug/ml. The slope of the scatter plot was close to unity, the intercept negligible, and the correlation coefficient was 0.99, all of which indicate that the method produces results equivalent to the reference method.

EXAMPLE VI

THEOPHYLLINE PROTECTED BINDING ASSAY USING MONOCLONAL ANTIBODIES

The experiments reported here compare polyclonal and monoclonal antibodies in the theophylline Protected Binding Assay. All of the materials, preparations and procedures were identical to those described in Example V, with the addition that monoclonal mouse anti-theophylline was also purchased from Kallestad, Austin, TX.

Results

Figure 8:
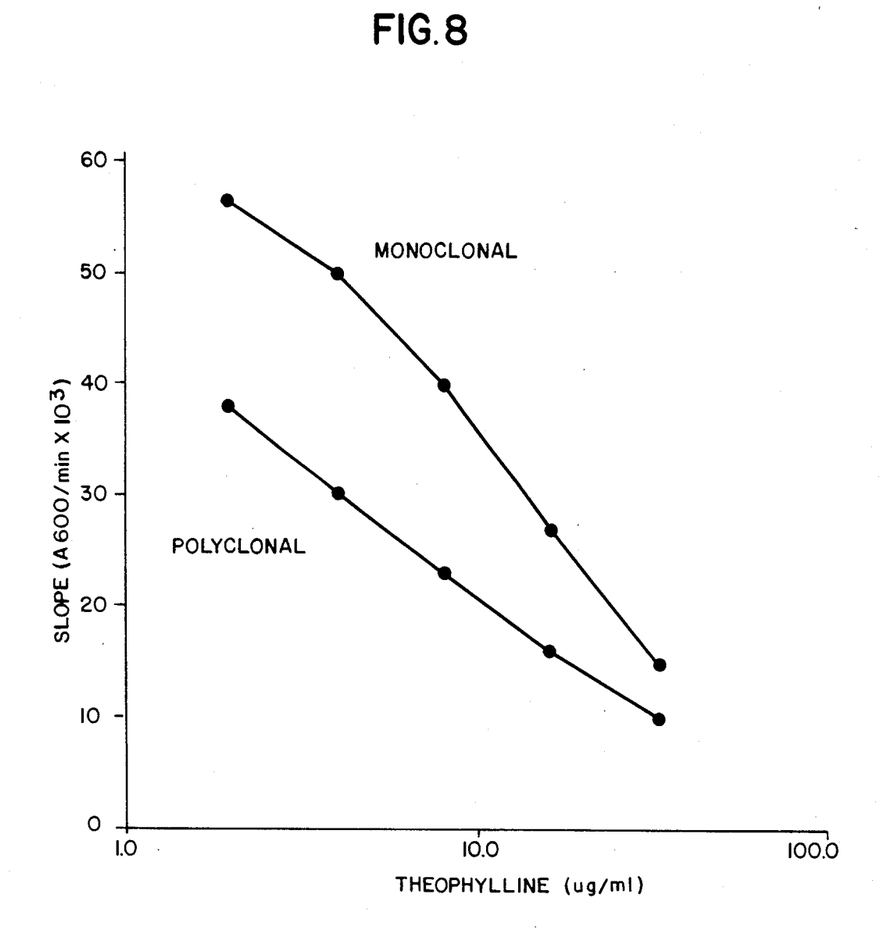
FIG. 8 is a graphical illustration of the absorbance at various theophylline levels using the Protected Binding Assay of the invention incorporating either polyclonal or monoclonal antibody, based on the experiments in Example VI.

The dose response curves obtained with the polyclonal and monoclonal antibodies are shown in FIG. 8. The two antibodies show similar dynamic range and sensitivies when used in the assay of the invention.

Conclusion

Polyclonal and monoclonal antibodies may be used in the assay of the invention.

What is claimed is:

1. A specific binding assay test composition for determination of an enzyme-resistant ligand in a sample wherein non-specific protein interference is avoided, which test composition comprises:
   (a) a solid phase incorporated with one partner of a specific binding pair comprising (1) said ligand or a binding analog of said ligand and (2) a specific binding protein for said ligand;
   (b) a conjugate comprising the other partner of said specific binding pair which is covalently bound to a substance which protects the specific binding protein of said pair from enzyme inactivation when bound with its partner; and
   (c) an active protein-inactivating enzyme.

2. The composition of claim 1 wherein said solid phase incorporated with a specific binding partner comprises a particle having a specific binding protein surface moiety.

3. The composition of claim 1 wherein said solid phase incorporated with a specific binding partner comprises a substrate particle bound to a specific binding protein.

4. The composition of claim 3 wherein said substrate particle is selected from the group consisting of eucaryotic cells, procaryotic cells and synthetic particles.

5. The composition of claim 4 wherein said synthetic particles are latex.

6. The composition of claim 1 wherein said specific binding protein is an antibody.

7. The composition of claim 6 wherein said antibody is specific to triiodothyronine.

8. The composition of claim 6 wherein said antibody is specific to thyroxine.

9. The composition of claim 6 wherein said antibody is present in a concentration of at least about 0.04 percent.

10. The composition of claim 9 wherein said antibody is present in a concentration of from about 0.04 to about 0.07 percent.

11. The composition of claim 1 wherein said conjugate of said enzyme-resistant ligand comprises a ligand or specific binding analog thereof incorporated with a high molecular weight carrier.

12. The composition of claim 11 wherein said conjugate comprises a ligand or specific binding analog thereof covalently bound with a high molecular weight carrier.

13. The composition of claim 12 wherein said high molecular weight carrier is a polymer.

14. The composition of claim 13 wherein said polymer is dextran.

15. The composition of claim 13 wherein said polymer is the cross-linking product of epichlorohydrin and sucrose.

16. The composition of claim 11 wherein said ligand is triiodothyronine.

17. The composition of claim 11 wherein said ligand is thyroxine.

18. The composition of claim 1 wherein said protein-inactivating enzyme is trypsin.

19. The composition of claim 1 wherein said protein-inactivating enzyme is pepsin.

20. The composition of claim 1 wherein said protein-inactivating enzyme is present in a concentration of not more than about 4.0 milligrams per milliliter.

21. The composition of claim 20 wherein said protein-inactivating enzyme is present in a concentration of from about 2.0 to about 4.0 milligrams per milliliter.

22. A specific binding assay test composition for thyroxine or triiodothyronine, which composition comprises:
 (a) particle-associated thyroxine or triiodothyronine antibody;
 (b) trypsin; and
 (c) a conjugate comprising thyroxine or triiodothyronine covalently bound with a high molecular weight polymer whereby non-specific protein interference is avoided.

23. The specific binding assay composition of claim 22 wherein
 (a) said particle-associated thyroxine or triiodothyronine antibody is present in a concentration of from about 0.04 to about 0.07 percent;
 (b) said trypsin is present in a concentration of from about 2.0 to about 4.0 milligrams per milliliter; and
 (c) said conjugate is present in a concentration of from about 0.22 to about 0.88 micrograms per milliliter.

24. A specific binding method of assaying for an enzyme-resistant ligand in a sample wherein non-specific protein interference is avoided, which method consists essentially of the steps of:
 (i) combining said sample in a reaction mixture with:
  (a) a solid phase incorporated with one partner of a specific binding pair comprising (1) said ligand or a binding analog of said ligand and (2) a specific binding protein for said ligand;
  (b) a conjugate comprising the other partner of said specific binding pair which is covalently bound to a substance which protects the specific binding protein of said pair from enzyme inactivation when bound with its partner; and
  (c) an active protein-inactivating enzyme; and
 (ii) detecting any resultant binding in said reaction mixture.

25. The method of claim 24 wherein said particle-associated specific binding protein comprises a particle having a specific binding protein surface moiety.

26. The method of claim 24 wherein said particle-associated specific binding protein comprises a substrate particle bound to a specific binding protein.

27. The method of claim 24 wherein said substrate particle is selected from the group consisting of eucaryotic cells, procaryotic cells and synthetic particles.

28. The method of claim 27 wherein said synthetic particles are latex particles.

29. The method of claim 24 wherein said specific binding protein is an antibody.

30. The method of claim 29 wherein said antibody is specific to triiodothyronine.

31. The method of claim 29 wherein said antibody is specific to thyroxine.

32. The method of claim 29 wherein said antibody is present in a concentration of at least about 0.04 percent.

33. The method of claim 32 wherein said antibody is present in a concentration of from about 0.04 percent to about 0.07 percent.

34. The method of claim 24 wherein said protein-inactivating enzyme is trypsin.

35. The method of claim 24 wherein said protein-inactivating enzyme is pepsin.

36. The method of claim 24 wherein said active protein-inactivating enzyme is present in a concentration of not more than about 4.0 milligrams per milliliter.

37. The method of claim 36 wherein said protein-inactivating enzyme is present in a concentration of from about 2.0 to about 4.0 milligrams per milliliter.

38. The method of claim 24 wherein said conjugate comprises an enzyme-resistant ligand or specific binding analog thereof incorporated with a high molecular weight carrier.

39. The method of claim 38 wherein said conjugate comprises a ligand or specific binding analog thereof covalently bound with a high molecular weight carrier.

40. The method of claim 39 wherein said high molecular weight carrier is a polymer.

41. The method of claim 40 wherein said polymer is dextran.

42. The method of claim 40 wherein said polymer is the cross-linking product of epichlorohydrin and sucrose.

43. The method of claim 38 wherein said ligand is triiodothyronine.

44. The method of claim 38 wherein said ligand is thyroxine.

45. A specific binding method of assaying for thyroxine or triiodothyronine in a sample wherein non-specific protein interference is avoided, which method consists essentially of
   (i) combining said sample in a reaction mixture with:
      (a) particle-associated thyroxine or triiodothyronine antibody;
      (b) a conjugate comprising thyroxine or triiodothyronine covalently bound with a high molecular weight polymer;
      (c) trypsin; and
   (ii) detecting any resultant binding in said reaction mixture.

46. The specific binding assay of claim 45 wherein:
   (a) said particle-associated thyroxine or triiodothyronine antibody is present in a concentration of from about 0.04 to about 0.07 percent;
   (b) said trypsin is present in a concentration of from about 2.0 to about 4.0 milligrams per milliliter; and
   (c) said conjugate is present in a concentration of from about 0.22 to about 0.88 micrograms per milliliter.

47. A test kit for use in determining a ligand in a sample by a specific binding assay method, which kit comprises the packaged combination of one or more components incorporated with:
   (a) a solid phase incorporated with one partner of a specific binding pair comprising (1) said ligand or a binding analog of said ligand and (2) a specific binding protein for said ligand;
   (b) a conjugate comprising the other partner of said specific binding pair which is covalently bound to a substance which protects the specific binding protein of said pair from enzyme inactivation when bound with its partner; and
   (c) an active protein-inactivating enzyme whereby non-specific protein interference is avoided.

* * * * *